US006949674B2

(12) United States Patent
Okanuma et al.

(10) Patent No.: US 6,949,674 B2
(45) Date of Patent: Sep. 27, 2005

(54) AROMATIC CARBOXYLIC ACIDS, ACID HALIDES THEREOF AND PROCESSES FOR PREPARING BOTH

(75) Inventors: Masako Okanuma, Jyoetsu (JP);
Yuichi Ishida, Shinagawa-ku (JP);
Yoko Hase, Susono (JP); Nobuhiro Higashida, Izumiohtsu (JP); Takashi Enoki, Yokohama (JP)

(73) Assignee: Sumitomo Bakelite Company, Ltd., Tokyo (JP)

( * ) Notice: Subject to any disclaimer, the term of this patent is extended or adjusted under 35 U.S.C. 154(b) by 9 days.

(21) Appl. No.: 10/432,516

(22) PCT Filed: Nov. 26, 2001

(86) PCT No.: PCT/JP01/10287

§ 371 (c)(1),
(2), (4) Date: Oct. 6, 2003

(87) PCT Pub. No.: WO02/42251

PCT Pub. Date: May 30, 2002

(65) Prior Publication Data

US 2004/0068139 A1 Apr. 8, 2004

(30) Foreign Application Priority Data

Nov. 27, 2000 (JP) ........................................ 2000-359089
Mar. 9, 2001 (JP) ........................................ 2001-067606

(51) Int. Cl.[7] ........................ C07C 63/33; C07C 63/337
(52) U.S. Cl. ........................ 562/452; 562/488; 562/840
(58) Field of Search .................................. 562/452, 488, 562/840

(56) References Cited

U.S. PATENT DOCUMENTS

| 4,587,312 A | * | 5/1986 | Hergenrother et al. ...... 525/535 |
| 4,622,182 A | * | 11/1986 | Hergenrother et al. ...... 562/855 |
| 6,518,390 B2 | | 2/2003 | Okanuma et al. |
| 2002/0013443 A1 | | 1/2002 | Okanuma et al. |

FOREIGN PATENT DOCUMENTS

| EP | 1 327 653 A1 | 7/2003 |
| JP | 62-292834 | 12/1987 |

OTHER PUBLICATIONS

International Search Report, dated Mar. 12, 2002, issued by the Japanese Patent Office, for International Patent No. PCT/JP01/10287 (2 pages).
International Search Report, dated Mar. 12, 2002, issued by the Japanese Patent Office, for International Patent No. PCT/US01/10287 (2 pages).

Crisp, Geoffrey T. et al., "Palladium–Catalysed Coupling of Terminal Alkynes with Aryl Halides Aided by Catalytic Zinc," Journal of Organometallic Chemistry, 1998, pp. 219–224, vol. 570, No. 2, Elsevier Science S.A. (6 pages).

* cited by examiner

*Primary Examiner*—Cecilia J. Tsang
*Assistant Examiner*—Taylor Victor Oh
(74) *Attorney, Agent, or Firm*—Smith, Gambrell & Russell, LLP

(57) ABSTRACT

A novel aromatic carboxylic acid useful as a material for macromolecular compounds and, in particular, for polycondensed macromolecular compounds exhibiting excellent heat resistance, an acid halide derivative thereof and a process for producing these compounds are disclosed. The aromatic carboxylic acid and the acid halide derivative thereof have structures represented general formulae (1) and (2), respectively, and can be efficiently produced from a dialkyl ester derivative of isophthalic acid and an acetylene derivative in accordance with the disclosed process comprising specific steps.

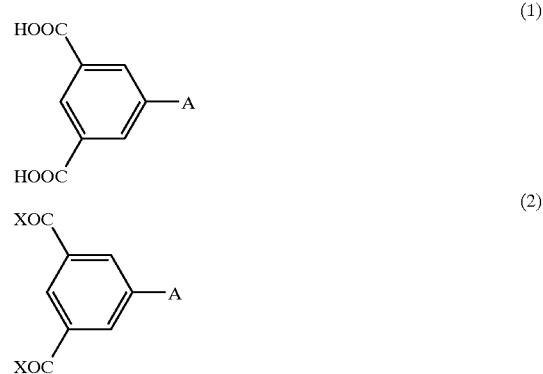

In the above formulae, A represents:

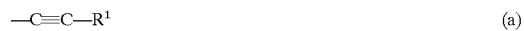

or

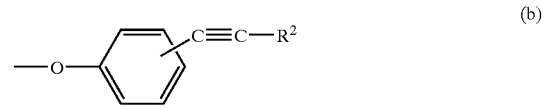

($R^1$ represents hydrogen atom, an alkyl group or an aromatic group, $R^2$ represents an alkyl group or an aromatic group) and X represents a halogen atom.

11 Claims, No Drawings

AROMATIC CARBOXYLIC ACIDS, ACID HALIDES THEREOF AND PROCESSES FOR PREPARING BOTH

TECHNICAL FIELD

The present invention relates to an aromatic carboxylic acid, an acid halide derivative thereof and a process for producing these compounds. More particularly, the present invention relates to an aromatic carboxylic acid useful as a material for macromolecular compounds and, in particular, for polycondensed macromolecular compounds exhibiting excellent heat resistance, an acid halide derivative thereof and a process for efficiently producing these compounds.

BACKGROUND ART

Aromatic carboxylic acids having two carboxyl groups in one molecule and acid halides of these compounds are used as the material for aromatic polyamide resins, polyarylate resins, polybenzoxazole resins and polybenzothiazole resins. Resins having various structures are produced and used in accordance with the applications.

In general, these resins have excellent heat resistance although these resins are thermoplastic macromolecular compounds and these resins are frequently used for applications exposed to high temperatures. As the means of further enhancing the heat resistance, introduction of thermosetting substituents has been attempted. Therefore, a material used for such resins has been desired.

DISCLOSURE OF THE INVENTION

Under the above circumstances, the present invention has a first object of providing an aromatic carboxylic acid useful as a material for macromolecular compounds and, in particular, for polycondensed macromolecular compounds exhibiting excellent heat resistance and an acid halide derivative thereof and has a second object of providing a process for efficiently producing these compounds.

As the result of extensive studies by the present inventors to achieve the above objects, it was found that the first object could be achieved by an aromatic carboxylic acid having a specific structure and an acid halide derivative thereof and that the second object could be achieved by efficiently producing these compounds in accordance with specific steps. The present invention has been completed based on the above knowledge.

The present invention provides:

(1) An aromatic carboxylic acid having a structure represented by general formula (1):

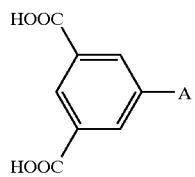

(1)

wherein A represents a group represented by general formula (a) or (b):

(a)

(b)

$R^1$ in general formula (a) representing hydrogen atom, an alkyl group or an aromatic group and $R^2$ in general formula (b) representing an alkyl group or an aromatic group;

(2) An acid halide derivative of an aromatic carboxylic acid having a structure represented by general formula (2):

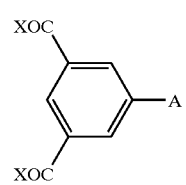

(2)

wherein A represents a group represented by general formula (a) or (b):

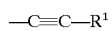

(a)

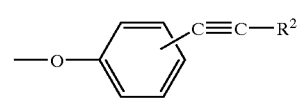

(b)

$R^1$ in general formula (a) representing hydrogen atom, an alkyl group or an aromatic group and $R^2$ in general formula (b) representing an alkyl group or an aromatic group; and X represents a halogen atom;

(3) A process for producing an aromatic carboxylic acid represented by general formula (1-1):

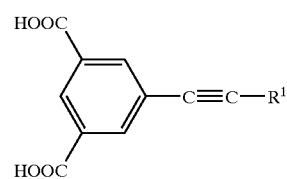

(1-1)

wherein $R^1$ represents hydrogen atom, an alkyl group or an aromatic group, which comprises:

obtaining a compound represented by general formula (5):

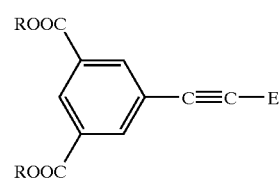

(5)

wherein R represents a lower alkyl group and E represents trimethylsilyl group, hydroxypropyl group, an alkyl group or an aromatic group, by reacting a compound represented by general formula (3):

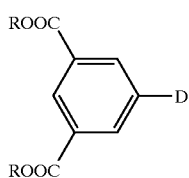

(3)

wherein D represents a group to be eliminated and R is as defined above, with a compound represented by general formula (4):

$$HC\equiv C-E \quad (4)$$

wherein E is as defined above;

forming a compound represented by general formula (6):

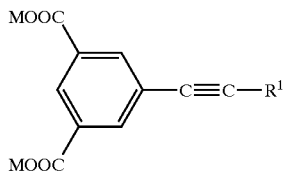

(6)

wherein $R^1$ is as defined above and M represents an alkali metal, by treating the obtained compound represented by general formula (5) in a presence of an alkali metal hydroxide; and treating the formed compound represented by general formula (6) with an acid;

(4) A process for producing an aromatic carboxylic acid represented by general formula (1-2):

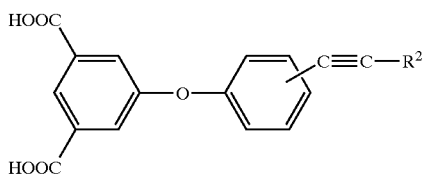

(1-2)

wherein $R^2$ represents an alkyl group or an aromatic group, which comprises:

obtaining a compound represented by general formula (9):

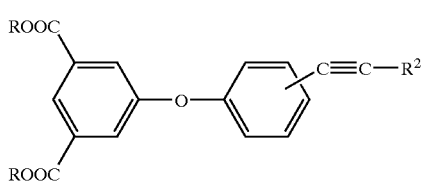

(9)

wherein R represents a lower alkyl group and $R^2$ is as defined above, by reacting a compound represented by general formula (7):

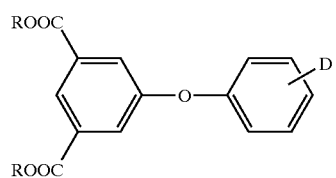

(7)

wherein D represents a group to be eliminated and R is as defined above, with a compound represented by general formula (8):

$$HC\equiv C-R^2 \quad (8)$$

wherein $R^2$ is as defined above;

forming a compound represented by general formula (10):

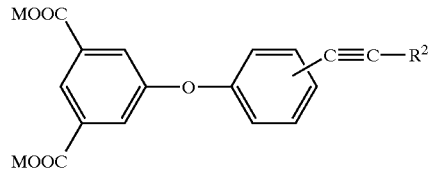

(10)

wherein $R^2$ is as defined above and M represents an alkali metal, by treating the obtained compound represented by general formula (9) in a presence of an alkali metal hydroxide; and treating the formed compound represented by general formula (10) with an acid;

(5) A process for producing an acid halide derivative of an aromatic carboxylic acid represented by general formula (2-1):

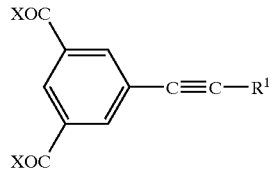

(2-1)

wherein X represents a halogen atom and $R^1$ represents hydrogen atom, an alkyl group or an aromatic group, which comprises treating with a halogenating agent a compound represented by general formula (1-1):

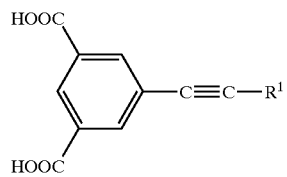

(1-1)

wherein $R^1$ is as defined above, or a compound represented by general formula (6):

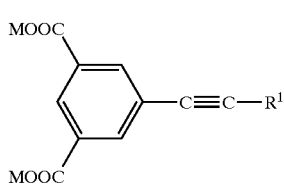
(6)

wherein M represents an alkali metal and $R^1$ is as defined above; and (6) A process for producing an acid halide derivative of an aromatic carboxylic acid represented by general formula (2-2):

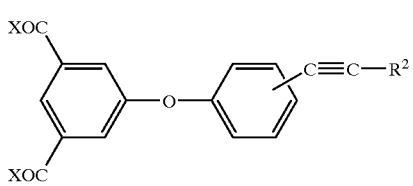
(2-2)

wherein X represents a halogen atom and $R^2$ represents an alkyl group or an aromatic group, which comprises treating with a halogenating agent a compound represented by general formula (1-2):

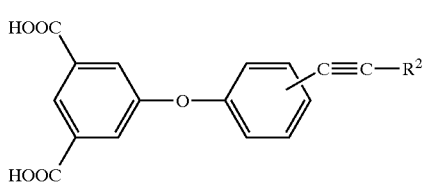
(1-2)

wherein $R^2$ is as defined above, or a compound represented by general formula (10):

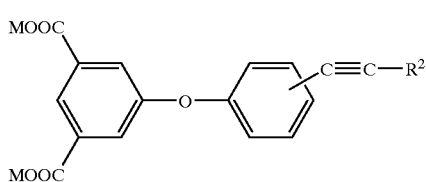
(10)

wherein M represents an alkali metal and $R^2$ is as defined above.

THE MOST PREFERRED EMBODIMENT TO CARRY OUT THE INVENTION

The aromatic carboxylic acid and the acid halide derivative of the aromatic carboxylic acid are novel compounds which are not described in literatures and are represented by general formula (1) and general formula (2), respectively:

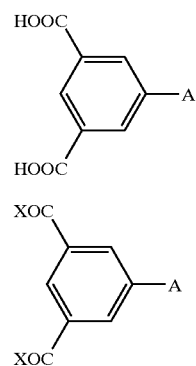
(1)

(2)

In the above general formulae (1) and (2), A represents a group represented by general formula (a) or (b):

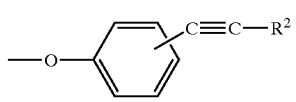
(a)

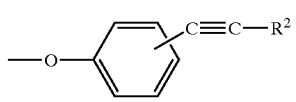
(b)

wherein $R^1$ represents hydrogen atom, an alkyl group or an aromatic group and $R^2$ represents an alkyl group or an aromatic group. In general formula (2), X represents a halogen atom.

The aromatic carboxylic acid represented by general formula (1) includes an aromatic carboxylic acid represented by general formula (1-1):

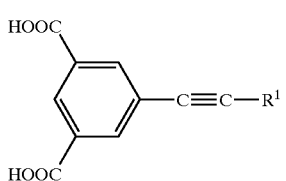
(1-1)

wherein $R^1$ is as defined above, and an aromatic carboxylic acid represented by general formula (1-2):

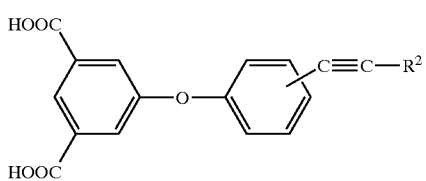
(1-2)

wherein $R^2$ is as defined above. The acid halide of an aromatic carboxylic acid represented by general formula (2) includes an acid halide derivative of an aromatic carboxylic acid represented by general formula (2-1):

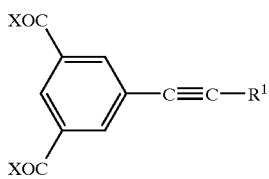
(2-1)

wherein R¹ and X are as defined above, and an acid halide derivative of an aromatic carboxylic acid represented by general formula (2-2):

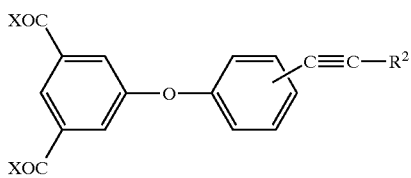
(2-2)

wherein R² and X are as defined above.

It is preferable from the standpoint of the practical use that the acid halides of aromatic carboxylic acids represented by general formulae (2-1) and (2-2) are acid chloride derivatives represented by general formulae (2-1) and (2-2), respectively, in which X represents chlorine atom.

Examples of the alkyl group and the aromatic group represented by R¹ and R² in general formulae (1) and (2) include alkyl groups such as ethyl group, propyl group and butyl group and aromatic group such as phenyl group, naphthyl group, anthryl group, quinolyl group and quinoxalyl group.

The process for producing these compounds will be described in the following.

The aromatic carboxylic acid represented by general formula (1-1) and the acid halide of an aromatic carboxylic acid represented by general formula (2-1) can be produced in accordance with the following route.

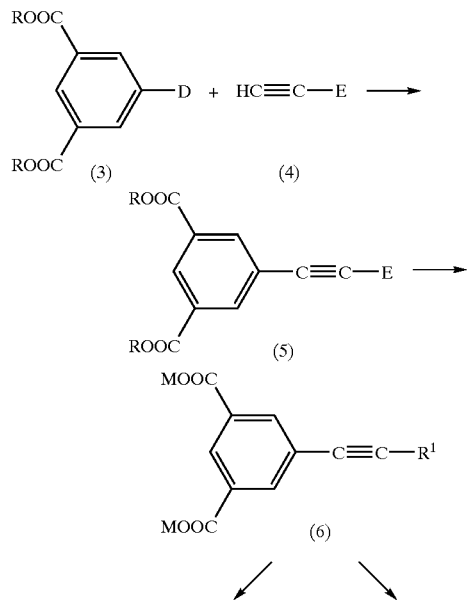

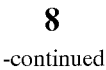
-continued

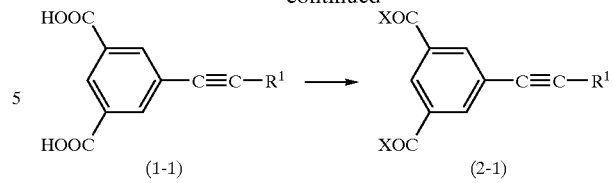

In general formula (3), D represents a group to be eliminated. In general formulae (3) and (5), R represents a lower alkyl group and preferably methyl group. In general formulae (4) and (5), E represents trimethylsilyl group, hydroxypropyl group, an alkyl group or an aromatic group. In general formula (6), M represents an alkali metal. In general formulae (6), (1-1) and (2-1), R¹ represents hydrogen atom, an alkyl group or an aromatic group. In general formula (2-1), X represents a halogen atom and preferably chlorine atom.

The dialkyl ester compound of isophthalic acid represented by general formula (3) in which the 5-position on the benzene ring is substituted with the group to be eliminated represented by D and the compound represented by general formula (4) in which one side of acetylene is substituted with a group represented by E are used as the starting materials and subjected to the coupling reaction and the compound represented by general formula (5) is obtained. It is preferable that a catalyst is used in the coupling reaction and, for example, a catalyst of a transition metal such as palladium can be used. As the group to be eliminated represented by D, a group eliminated easily from the aromatic ring by the coupling reaction in the presence of the above catalyst is preferable. Examples of the group to be eliminated include halogen atoms such as fluorine atom, chlorine atom, bromine atom and iodine atom and trifluoromethanesulfonyloxy group. As the substituent represented by E, a group working as a protective group can be used and preferable examples of such a group include trimethylsilyl group and hydroxypropyl group. Examples of the substituent represented by E include aromatic groups and alkyl groups. Examples of the aromatic group include phenyl group, naphthyl group, anthryl group, quinolyl group and quinoxalyl group.

The alkyl group is eliminated from the carboxylic acid ester group in this compound in the presence of an alkali metal hydroxide and, at the same time, the protective group is eliminated when the group represented by E is the protective group in the compound represented by general formula (5). Thus, an alkali metal salt of a derivative of isophthalic acid represented by general formula (6) can be obtained.

The aromatic carboxylic acid represented by general formula (1-1) can be obtained by treating the alkali metal salt of a derivative of isophthalic acid represented by general formula (6) with an acid. The acid halide derivative and preferably the acid chloride derivative represented by general formula (2-1) can be obtained by treating the alkali metal salt of a derivative of isophthalic acid represented by general formula (6) with a halogenating agent and preferably with a chlorinating agent.

In the case of the dialkyl ester of isophthalic acid represented by general formula (3) in which the 5-position on the benzene ring is substituted with the group represented by D, when the group to be eliminated represented by D is trifluoromethanesulfonyloxy group, a dialkyl ester of 5-trifluoromethanesulfonyloxyisophthalic acid [formula (3-1)] is obtained by esterification of a dialkyl ester of 5-hydroxyisophthalic acid [formula (11)] with trifluoromethanesulfonic acid anhydride [formula (12)] in accordance with the following reaction equation:

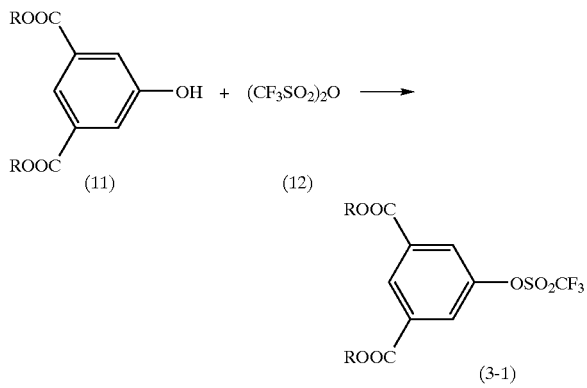

wherein R represents a lower alkyl group.

As shown in the following reaction equation:

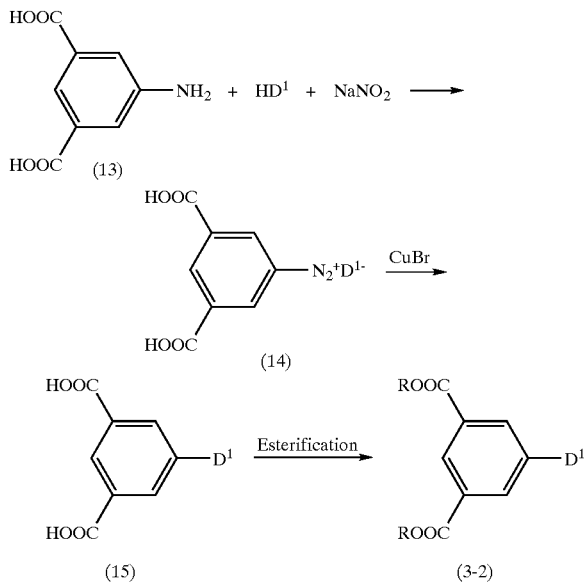

wherein $D^1$ represents a halogen atom and R represents a lower alkyl group, an isophthalic acid (15) in which the group to be eliminated is a halogen can be produced using 5-aminoisophthalic acid [formula (13)] as the raw material in accordance with the Sandmeyer reaction which proceeds via a diazonium salt [formula (14)]. Then, a dialkyl ester of isophthalic acid represented by formula (3-2) in which the group to be eliminated represented by D is a halogen is easily obtained by converting the carboxylic acid into an alkyl ester.

Embodiments of the processes for producing the aromatic carboxylic acid represented by general formula (1-1) and the acid halide derivative of the aromatic carboxylic acid represented by general formula (2-1) will be described in the following.

As an embodiment using a dialkyl ester of 5-bromoisophthalic acid [D=Br in formula (3)], diazonium hydrobromide [$D^1$=Br in Formula 14] is obtained by the reaction of 5-aminoisophthalic acid [formula 13], hydrobromic acid and sodium nitrite. By the reaction of the obtained product with cuprous bromide, nitrogen gas is generated and 5-bromoisophthalic acid [$D^1$=Br in formula (15)] is obtained. Then, under the atmosphere of an inert gas such as nitrogen, argon and helium, a lower alcohol is added in the presence of an acidic catalyst such as sulfuric acid and the resultant mixture is heated under the refluxing condition. Esterification takes place between the lower alcohol and the carboxylic acid and the dialkyl ester of 5-bromoisophthalic acid [$D^1$=Br in formula (3-2)] is obtained. In this reaction, it is preferable that the lower alcohol is used in a greatly excess amount so that the equilibrium of the reaction shifts to the side of the product. It is preferable that the lower alcohol is distilled in advance so that the amount of water in the reaction system is decreased.

When a dialkyl ester of 5-trifluoromethanesulfonyloxyisophthalic acid [D=trifluoromethanesulfonyloxy group in formula (3)] is used, a dialkyl ester of 5-hydroxyisophthalic acid [formula (11)] and a base are dissolved into a solvent. To the resultant solution cooled at −78 to 10° C., trifluoromethanesulfonic acid anhydride [formula (12)] is added and the reaction is allowed to proceed at a temperature in the range of 0° C. to about the boiling point of the solvent. The time of the reaction is not limited. In the above reaction, the reaction solution is cooled before the addition of trifluoromethanesulfonic acid anhydride since the reaction is an exothermic reaction and, when the temperature exceeds the range described above, the reaction proceeds rapidly and there is the possibility that bumping of the solvent takes place. By treating the reaction product thus obtained by the conventional operation of separation such as the extraction and the phase separation, the dialkyl ester of 5-trifluoromethanesulfonyloxyisophthalic acid can be obtained.

The obtained compound may be further purified in accordance with the recrystallization or the column chromatography.

It is preferable that trifluoromethanesulfonic acid anhydride is used in an amount by equivalent 1 to 1.5 times the amount by equivalent of the dialkyl ester of 5-hydroxyisophthalic acid.

As the base, tertiary amines having no active hydrogen are preferable. Examples of the tertiary amine include pyridines such as pyridine and methylpyridine and trialkylamines such as triethylamine and tributylamine. It is preferable that the tertiary amine is used in an amount by equivalent 1 to 1.5 times the total amount by equivalent of the dialkyl ester of 5-hydroxyisophthalic acid and trifluoromethanesulfonic acid anhydride.

Examples of the solvent include aromatic hydrocarbons, hydrocarbons, ethers and halogenated hydrocarbons which are inert to the reaction such as benzene, toluene, n-hexane, cyclohexane, petroleum ether, ethyl ether, tetrahydrofuran, dichloromethane, 1,2-dichloromethane and chloroform. The solvent may be used singly or in combination of two or more. The amount of the solvent is not particularly limited.

When water is present in the solvent, side reactions with trifluoromethanesulfonic acid anhydride of the reacting reagent takes place and the actual relative amounts by equivalent of the reacting species in the reaction change. Therefore, it is preferable that the anhydrous solvent is used or that the amount of water is known in advance and the above compound is used in an amount greater than the theoretical amount so that the amount in the actual use is suitably adjusted.

In the process for obtaining the compound represented by general formula (5), a reaction product is obtained by the coupling reaction of the dialkyl ester of 5-bromoisophthalic acid or the dialkyl ester of 5-trifluorosulfonyloxyisophthalic acid obtained above and the compound obtained by substituting one side of acetylene with a protective group represented by E or an alkyl group or an aromatic group represented by E which is represented by general formula (4) in the presence of a catalyst under the atmosphere of an inert gas such as nitrogen, argon and helium at a temperature in the range of about 20 to 150° C. The time of the above reaction is not particularly limited. The compound represented by general formula (5) can be obtained by treating the reaction product obtained as described above by an operation of separation such as concentration and reprecipitation. The obtained compound may be purified in accordance with the column chromatography or recrystallization, where necessary.

The compound obtained by substituting one side of acetylene with a protective group represented by E which is represented by general formula (4) is not particularly limited as long as the protective group E can be eliminated with hydroxide of an alkali metal. Trimethylsilylacetylene in which the protective group is trimethylsilyl group and 3-methyl-1-butyn-3-ol in which the protective group is hydroxypropyl group are preferable. On calculation, it is sufficient that the amount equivalent to the compound represented by general formula (3) is used. However, it is preferable that the amount by equivalent is adjusted within the range of 1 to 2 times the amount by equivalent of the compound represented by general formula (3) so that the reaction can proceed completely.

In general, the catalyst system is not particularly limited as long as the carbon-carbon bond can be formed. A catalyst system comprising dichlorobis(triphenylphosphine) palladium, copper iodide and triphenyl-phosphine are preferable. The amount of dichlorobis(triphenyl-phosphine) palladium is not particularly limited. It is preferable that dichlorobis(triphenylphosphine)palladium is used in an amount in the range of 0.1 to 1% by mole based on the amount of the compound represented by general formula (5) and that triphenylphosphine is used in an amount by equivalent in the range of 1 to 20 times the amount by equivalent of dichlorobis(triphenylphosphine)palladium and copper iodide is used in an amount by equivalent in the range of 1 to 5 times the amount by equivalents of dichlorobis(triphenylphosphine)palladium.

As the solvent used for the above reaction, an amine-based solvent is preferable so that the catalytic reaction is promoted by catching the formed acid. Examples of the solvent include diethylamine, butylamine, tertiary amines such as triethylamine and tributylamine and cyclic amines such as pyridine and piperidine. The solvent may be used singly or in combination of two or more. The amount of the solvent is not particularly limited. It is preferable that the amount by weight of the solvent is in the range of 2 to 50 times the amount by weight of the material. It is preferable that the solvent is distilled in advance so that side reactions and deactivation of the catalyst are prevented.

In the process for obtaining the alkali metal salt of the isophthalic acid derivative represented by general formula (6), a reaction product is obtained by dealkylation of the carboxylic acid ester by treating the compound represented by general formula (5) in the presence of an alkali metal hydroxide in a solvent and simultaneous elimination of protection of ethynyl group when the group represented by E in the compound represented by general formula (5) is a protective group such as trimethylsilyl group and hydroxypropyl group,. The temperature and the time of the reaction are not particularly limited. It is preferable that the temperature is in the range of the room temperature to the temperature of refluxing of the solvent. The crystals formed by cooling the obtained reaction product are separated, washed with an alcohol-based solvent such as methanol, ethanol, butanol and isopropanol and dried and the alkali metal salt of the isophthalic acid derivative represented by general formula (6) can be obtained.

As the alkali metal hydroxide, potassium hydroxide and sodium hydroxide are preferable. It is preferable that the amount by equivalent of the alkali metal hydroxide is 3 times the amount by equivalent or more of the compound represented by general formula (5).

The solvent for the reaction is not particularly limited as long as the solvent is not an ester reacting with the alkali metal hydroxide. Alcohol-based solvents having a great solubility for alkali metal hydroxides such as methanol, ethanol, butanol and isopropanol are preferable. The amount of the solvent is not particularly limited. From the standpoint of the easiness of the operation, it is preferable that the amount by weight is in the range of 5 to 50 times the amount by weight of the compound represented by general formula (5).

The aromatic carboxylic acid represented by general formula (1-1) of the present invention can be obtained by dissolving the alkali metal salt of the isophthalic acid derivative obtained above [formula (6)] into water, obtaining precipitates by treating the obtained solution with an acid such as hydrochloric acid, sulfuric acid and nitric acid until the solution becomes acidic, preferably, until the pH becomes 1, separating the obtained precipitates by filtration and washing and drying the separated precipitates. It is preferable that the treatments are completed in a short time since side reactions of the ethynyl portion such as addition and polymerization may occasionally take place when the compound is exposed to a strong acid for a long time.

The acid halide derivative of the carboxylic acid represented by general formula (2-1) of the present invention can be obtained by reacting the alkali metal salt of the isophthalic acid derivative obtained above [formula (6)] with a halogenating agent at a temperature in the range of about 0 to 70° C. in a solvent or using the halogenating agent in an excess amount as the solvent, removing the solvent from the resultant reaction mixture, washing the obtained solid product with the solvent and recrystallizing the washed product. In place of the alkali metal salt of the isophthalic acid derivative represented by general formula (6), the aromatic carboxylic acid represented by general formula (1-1) may be used.

As the halogenating agent, thionyl halides and oxalyl halides are preferable. The amount by weight of the halogenating agent is, in general, 2 times the amount by weight of the alkali metal salt of the isophthalic acid derivative represented by general formula (6) or more. There is no upper limit in the amount. When no solvent is used, the halogenating agent may be used in a greatly excess amount such as an amount by equivalent 10 times the amount by equivalent of the above compound or more.

The solvent is not particularly limited. Examples of the solvent include aromatic hydrocarbons such as benzene, toluene and xylene, hydrocarbons such as pentane, hexane, cyclohexane and petroleum ether, and halogenated hydrocarbons such as dichloromethane, chloroform, carbon tetrachloride, 1,2-dichloroethane and chlorobenzene. The solvent can be used in a desired amount relative to the amount of the alkali metal salt of the isophthalic acid derivative represented by general formula (6).

In the above treatments, a based such as N,N-dimethylformamide and pyridine may be added to promote the reaction.

A polymerization inhibitor such as hydroquinone and hydroquinone monomethyl ether may be added to suppress the polymerization at the ethynyl portion.

By treating the aromatic carboxylic acid represented by general formula (1-1), which is obtained by treating the alkali metal salt of the isophthalic acid derivative represented by general formula (6) with an acid, with the halogenating agent, the acid halide derivative represented by general formula (2-1) can be obtained. As the halogenating agent, a chlorinating agent is preferable from the standpoint of the practical use.

The aromatic carboxylic acid represented by general formula (1-2) and the acid halide derivatives of the aromatic carboxylic acid represented by general formula (2-2) can be produced in accordance with the following route.

preferably chlorine atom. In these general formulae, R represents a lower alkyl group and preferably methyl group.

By the reaction of forming the ether bond between the dialkyl ester of 5-hydroxyisophthalic acid represented by formula (11) and fluoronitrobenzene represented by formula (16) as the starting materials using a base such as potassium carbonate and sodium carbonate, the dialkyl ester of 5-(nitrophenoxy)isophthalic acid represented by formula (17) can be obtained.

By treating this compound with palladium-active carbon or platinum-active carbon under the atmosphere of hydrogen or by treating this compound with tin or tin chloride under the acidic condition, the dialkyl ester of 5-(aminophenoxy)isophthalic acid represented by formula (18) can be obtained.

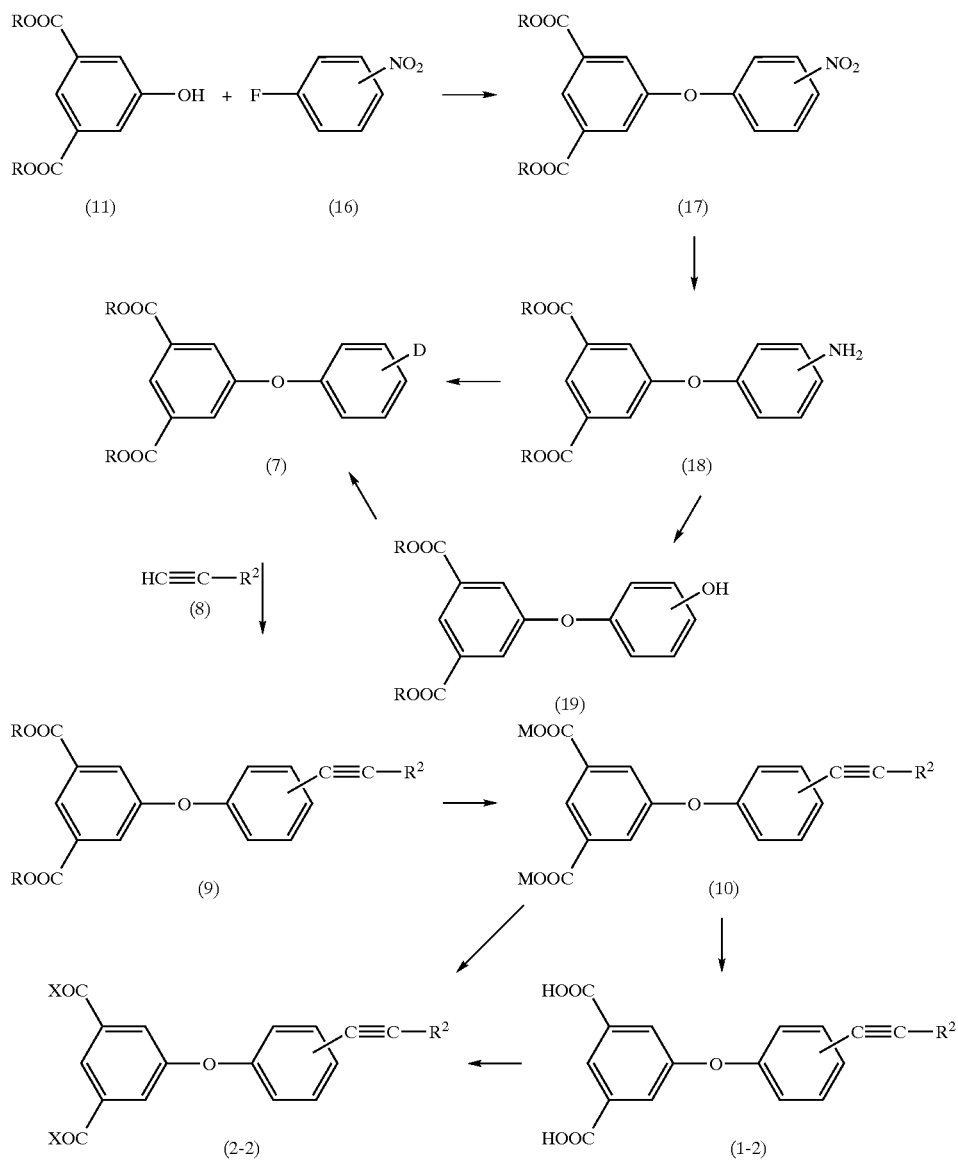

In general formula (7), D represents a group to be eliminated. In general formulae (8), (9), (10), (1-2) and (2-2), $R^2$ represents an alkyl group or an aromatic group. In general formula (10), M represents an alkali metal. In general formula (2-2), X represents a halogen atom and By diazotization of this compound by adding sodium nitrite in an acidic solution, followed by addition of potassium iodide, sodium iodide, copper bromide or copper chloride, a dialkyl ester of 5-(iodophenoxy)-isophthalic acid, a dialkyl ester of 5-(bromophenoxy)isophthalic acid or a dialkyl ester of 5-(chlorophenoxy)isophthalic acid, which are compounds represented by general formula (7) in which the group to be eliminated represented by D is a halogen atom, can be obtained.

As another process, by diazotizing the compound represented by formula (18) with sodium nitrite, followed by heating the obtained compound under an acidic condition, a dialkyl ester of 5-(hydroxy-phenoxy)isophthalic acid which is the compound represented by formula (19) is obtained. By esterification of this compound with trifluoromethanesulfonic acid anhydride, a dialkyl ester of 5-(trifluoro-methanesulfonyloxyphenoxy)isophthalic acid, which is the compound represented by general formula (7) in which the group to be eliminated represented by D is trifluoromethanesulfonyloxy group, is obtained.

In accordance with the same procedures as those described above, the compound represented by general formula (9) can be obtained by the coupling reaction of the dialkyl ester compound represented by general formula (7) and the compound represented by general formula (8) in which one side of the acetylene is substituted with the group represented by $R^2$. Examples of the group represented by $R^2$ include aromatic groups and alkyl groups. Examples of the aromatic group include phenyl group, naphthyl group, anthryl group, quinolyl group and quinoxalyl group. Examples of the alkyl group include ethyl group, propyl group and butyl group.

By dealkylation of the carboxylic acid ester group by treating the above compound with an alkali metal hydroxide, the alkali salt of the isophthalic acid represented by general formula (10) can be obtained.

By treating the alkali metal salt of the isophthalic derivative represented by general formula (10) with an acid, the aromatic carboxylic acid represented by general formula (1-2) can be obtained. By treating the above alkali metal salt with a halogenating agent and preferably with a chlorinating agent, the acid halide derivative, and preferably the acid chloride derivative, represented by general formula (2-2) can be obtained.

Embodiments of the process for producing the aromatic carboxylic acid represented by general formula (1-2) and the acid halide derivative of the aromatic carboxylic acid represented by general formula (2-2) will be described in the following.

In the present embodiment, the dialkyl ester of 5-(nitrophenoxy)-isophthalic acid represented by formula (17) can be obtained by the reaction of the dialkyl ester of 5-hydroxyisophthalic acid [formula (11)] and fluoronitrobenzene [formula (16)] in a polar solvent such as N,N-dimethyl-formamide, N,N-dimethylacetamide, N-methyl-2-pyrrolidone and dimethyl sulfoxide in the presence of a base such as potassium carbonate and sodium carbonate at a temperature in the range of about 100 to 200° C. In this reaction, the time of the reaction is not particularly limited. It is preferable that the base is used in an amount by equivalent 1 to 10 times the amount by equivalent of the dialkyl ester of 5-hydroxyisophthalic acid.

The dialkyl ester of 5-(aminophenoxy)isophthalic acid represented by formula (18) can be obtained by treating the dialkyl ester of 5-(nitrophenoxy)isophthalic acid [formula (17)] in a solvent such as tetrahydrofuran, a mixed solvent of tetrahydrofuran and ethanol (or another alcohol-based solvent such as methanol) and N,N-dimethylformamide under the atmosphere of hydrogen in the presence of a catalyst such as palladium-active carbon and platinum-active carbon. In this reaction, the time of the reaction and the amount of the solvent are not particularly limited. It is preferable that the catalyst is used in an amount of 0.1 to 10% by mole based on the amount of the dialkyl ester of 5-(aminophenoxy)isophthalic acid.

The dialkyl ester of 5-(aminophenoxy)isophthalic acid can be obtained also by treating the dialkyl ester of 5-(nitrophenoxy)isophthalic acid with tin or tin chloride under an acidic condition.

The dialkyl ester of 5-(iodophenoxy)isophthalic acid, which is the compound represented by general formula (7) in which the group to be eliminated represented by D is iodine atom, can be obtained by obtaining a diazonium salt of a mineral acid by the reaction of the dialkyl ester of 5-(aminophenoxy)isophthalic acid [formula (18)], an aqueous solution of the mineral acid and sodium nitrite, followed by the reaction of the diazonium salt with potassium iodide or sodium iodide accompanied with generation of nitrogen gas. Examples of the mineral acid include sulfuric acid, hydrochloric acid, nitric acid and hydrobromic acid. The amount of the mineral acid is not particularly limited. It is preferable that the sodium nitrite described above and potassium iodide or sodium iodide described above are used in an amount by equivalent 1 to 2 times the amount by equivalent of the dialkyl ester of 5-(aminophenoxy)isophthalic acid.

The dialkyl ester of 5-(bromophenoxy)isophthalic acid and the dialkyl ester of 5-(chlorophenoxy)isophthalic acid, which are the compounds represented by general formula (7) in which the group to be eliminated represented by D is bromine and chlorine, respectively, can be obtained in accordance with the above process using copper bromide and copper chloride, respectively, in place of potassium iodide or sodium iodide. To obtain the dialkyl ester of 5-(trifluoromethanesulfonyloxy-phenoxy)-isophthalic acid, in which the group to be eliminated represented by D is trifluoromethanesulfonyloxy group, a diazonium salt of a mineral acid is obtained by the reaction of the dialkyl ester of 5-(aminophenoxy)-isophthalic acid [formula (18)], the mineral acid and sodium nitrite and the dialkyl ester of 5-(hydroxyphenoxy)isophthalic acid [formula (19)] is obtained by heating the diazonium salt under an acidic condition.

Examples of the mineral acid include sulfuric acid, hydrochloric acid and nitric acid. The amount of the mineral acid is not particularly limited. It is preferable that the sodium nitrite is used in an amount by equivalent 1 to 2 times the amount by equivalent of the dialkyl ester of 5-(aminophenoxy)isophthalic acid.

Then, the dialkyl ester of 5-(hydroxyphenoxy)isophthalic acid [formula (19)] and hydrochloric acid are dissolved into a solvent. To the solution cooled at about −78 to 10° C. trifluoromethanesulfonic acid anhydride is added and the reaction is allowed to proceed at a temperature in the range of about 0° C. to the boiling point of the solvent. The reaction product thus obtained is treated by a conventional method of separation such as extraction, phase separation and concentration and the dialkyl ester of 5-(trifluoromethanesulfonyloxyphenoxy)isophthalic acid can be obtained.

Where necessary, the above product can be purified in accordance with recrystallization or the column chromatography.

It is preferable that trifluoromethanesulfonic acid anhydride is used in an amount by equivalent 1 to 1.5 times the amount by equivalent of the dialkyl ester of 5-(hydroxyphenoxy)isophthalic acid.

As the base described above, amines having no active hydrogen such as tertiary amines are preferable. Examples of the base include pyridines such as pyridine and methylpyridine and trialkylamines such as triethylamine and tributylamine. It is preferable that the base is used in an amount by equivalent 1 to 1.5 times the total amount by equivalent of the dialkyl ester of 5-(hydroxyphenoxy) isophthalic acid and trifluoro-methanesulfonic acid anhydride.

Examples of the above solvent include solvents inert to the reaction such as aromatic hydrocarbons, hydrocarbons, ethers and halogenated 5 hydrocarbons. Specific examples of the solvent include benzene, toluene, n-hexane, cyclohexane, petroleum ether, ethyl ether, tetrahydrofuran, dichloromethane, 1,2-dichloromethane and chloroform. The solvent may be used singly or in combination of two or more. The amount of the solvent is not particularly limited.

The compound represented by general formula (9) can be obtained by the coupling reaction of the dialkyl ester of 5-(iodophenoxy)isophthalic acid or the dialkyl ester of 5-(trifluoromethanesulfonyloxyphenoxy)-isophthalic acid which are obtained above with the compound represented by general formula (8) in which one side of acetylene is substituted with an alkyl group or an aromatic group represented by $R^2$ in accordance with the same process as that for the compound represented by general formula (5).

Examples of the compound represented by general formula (8) include ethynylbenzene, ethynylnaphthalene, ethynylanthracene, ethynyl-quinoline, ethynylquinoxaline, 1-butyne, 1-pentyne, 3,3-dimethyl-1-butyn and 1-hexyne. It is preferable that the above compound is used in an amount by equivalent 1 to 1.5 times the amount by equivalent of the compound represented by general formula (7).

The alkali metal salt of the isophthalic acid derivative represented by general formula (10) can be obtained by dealkylation of the compound represented by general formula (9) in accordance with the same process as that for the compound represented by general formula (6).

The amount by equivalent of the alkali metal hydroxide is, in general, 2 times the amount by equivalent of the compound represented by general formula (9) or more.

The aromatic carboxylic acid represented by general formula (1-2) can be obtained by the acidification of the alkali metal salt of the isophthalic acid derivative represented by general formula (10) in accordance with the same process as that for obtaining the aromatic carboxylic acid represented by general formula (1-1). The acid halide derivative of the aromatic carboxylic acid represented by general formula (2-2) can be obtained by the reaction of the alkali metal salt of the isophthalic acid derivative represented by general formula (10) with the halogenating agent in a solvent or using the halogenating agent in an excess amount as the solvent. The aromatic carboxylic acid represented by general formula (1-2) may be used in place of the alkali metal salt of the aromatic carboxylic acid represented by general formula (10). As the halogenating agent, the chlorinating agent is preferable from the standpoint of the practical use.

The present invention will be described more specifically with reference to examples in the following. However, the present invention is not limited to the examples.

To evaluate the properties of the obtained compounds, the measurements of the melting point and the spectra of $^1$H-NMR, $^{13}$C-NMR and MS and the elemental analysis were conducted. The conditions for the measurements of various properties were as follows.

Test Methods
(1) Melting Point

The melting point was measured by using a differential scanning calorimeter (DSC) of the DSC-200 type manufactured by SEIKO DENSHI Co., Ltd. under elevation of the temperature at a rate of 10° C./min.

(2) Nuclear Magnetic Resonance Spectroscopic Analysis ($^1$H-NMR and $^{13}$C-NMR)

The nuclear magnetic resonance spectra were obtained by using an apparatus of JNM-GSX400 type manufactured by NIPPON DENSHI Co., Ltd. $^1$H-NMR was conducted at a resonance frequency of 400 MHz and $^{13}$C-NMR was conducted at a resonance frequency of 100 MHz. As the solvent used in the measurement, deuterated dimethyl sulfoxide DMSO-$d_6$ was used for the measurement of 5-ethynylisophthalic acid as the deuterated solvent; deuterated acetone $(CD_3)_2CO$ was used for 5-(2-phenylethynyl) isophthalic acid as the deuterated solvent; and deuterated chloroform $CDCl_3$ was used for 5-ethynylisophthalic acid chloride and 5-(2-phenylethynyl)isophthalic acid chloride as the deuterated solvent.

(3) Infrared Spectroscopic Analysis (IR)

The infrared spectroscopic analysis was conducted by using an apparatus of the JIR-550 type manufactured by NIPPON DENSHI Co., Ltd. in accordance with the KBr tablet method.

(4) Mass Analysis (MS)

The mass analysis was conducted by using an apparatus of the JMS-700 type manufactured by NIPPON DENSHI Co., Ltd. in accordance with the field desorption method.

(5) Elemental Analysis

The elemental analysis of carbon and hydrogen was conducted using an apparatus of the 2400 type manufacture by PERKIN ELMER Company. The elemental analysis of chlorine was conducted in accordance with the method of combustion and titration in a flask.

EXAMPLE 1

[Preparation of dimethyl 5-trifluoromethanesulfonyloxyisophthalate from dimethyl 5-hydroxyisophthalate]

Into a 5 liter four-necked flask equipped with a thermometer, a Dimroth condenser, a calcium chloride tube and a stirrer, 190.0 g (0.904 moles) of dimethyl 5-hydroxyisophthalate, 3 liters of dehydrated toluene and 214.7 g (2.718 moles) of dehydrated pyridine were placed and the resultant mixture was cooled at −30° C. under stirring. To the cooled mixture, 510.2 g (1.808 moles) of anhydrous trifluoromethanesulfonic acid was slowly added dropwise with sufficient care so that the temperature did not exceed −25° C. It took 1 hour to complete the addition. After the addition was completed, the temperature of the reaction was elevated at 0° C. and the reaction was allowed to proceed for 1 hour. Then, the temperature was elevated to the room temperature and the reaction was allowed to proceed for 5 hours. The obtained reaction mixture was poured into 4 liters of ice water and separated into an aqueous layer and an organic layer. The aqueous layer was treated twice by extraction with 500 ml of toluene and the extract was combined with the organic layer. The obtained organic layer was washed twice with 3 liters of water and dried with 100 g of anhydrous magnesium sulfate. From the resultant mixture, anhydrous magnesium sulfate was removed by filtration and toluene was removed by distillation using a rotary evaporator. After drying under a reduced pressure, 294.0 g of dimethyl 5-trifluoromethanesulfonyloxyisophthalate was obtained as a light yellow solid substance (the yield: 95%). The crude product obtained above was recrystallized from hexane and white needle crystals were obtained. The obtained crystals were used for the next reaction.

[Preparation of 4-(3,5-bis(methoxycarbonyl)phenyl)-2-methyl-3-butyn-1-ol from dimethyl 5-trifluoromethanesulfonyloxyisophthalate]

Into a 1 liter four-necked flask equipped with a thermometer, a Dimroth condenser, an inlet for nitrogen and a stirrer, 125 g (0.365 moles) of dimethyl 5-trifluoromethanesulfonyloxyisophthalate obtained above, 1.1 g (0.00419 moles) of triphenylphosphine, 0.275 g (0.00144 moles) of copper iodide and 33.73 g (0.401 moles) of 3-methyl-1-butyn-3-ol were placed and nitrogen was introduced. To the obtained mixture, 375 ml of dehydrated triethylamine and 200 ml of dehydrated pyridine were added and dissolved under stirring. After the introduction of nitrogen was continued for 1 hour, 0.3 g (0.000427 moles) of dichlorobis(triphenylphosphine)palladium was quickly added and the resultant mixture was heated in an oil bath for 1 hour under the refluxing condition. Then, triethylamine and pyridine were removed by distillation under a reduced pressure and a viscous brown solution was obtained. The obtained solution was poured into 500 ml of water. The formed solid substance was separated by filtration and washed twice with each of 500 ml of water, 500 ml of a 5 moles/liter hydrochloric acid and 500 ml of water. The solid substance was dried at 50° C. under a reduced pressure and 98.8 g of 4-(3,5-bis(methoxycarbonyl)-phenyl)-2-methyl-3-butyn-1-ol was obtained (the yield: 98%).

[Preparation of Dipotassium 5-ethynylisophthalate from 4-(3,5-bis(methoxycarbonyl)phenyl)-2-methyl-3-butyn-1-ol]

Into a 5 liter four-necked flask equipped with a thermometer, a Dimroth condenser and a stirrer, 3 liters of n-butanol and 182 g (2.763 moles) of potassium hydroxide (85%) were placed and dissolved by heating under the refluxing condition. To the obtained solution, 95 g (0.344 moles) of 4-(3,5-bis(methoxycarbonyl)phenyl)-2-methyl-3-butyn-1-ol synthesized above was added and the resultant mixture was heated for 30 minutes under the refluxing condition. The reaction mixture was then cooled in an ice bath and the formed crystals were separated by filtration. The crystals were washed twice with 1 liter of ethanol and dried at 60° C. under a reduced pressure and 88.87 g of dipotassium 5-ethynyl-isophthalate was obtained (the yield: 97%).

[Preparation of 5-ethynylisophthalic acid from dipotassium 5-ethynyl-isophthalate]

Dipotassium 5-ethynylisophthalate in an amount of 5 g (0.019 moles) was dissolved into 20 ml of ion-exchanged water and insoluble substances were removed by filtration with a 5C filter paper. To the obtained filtrate, a 5 moles/liter hydrochloric acid was added under stirring until the pH became 1. The formed solid substance was separated by filtration, washed with ion-exchanged water and filtered. The filtration and the washing were repeated twice. The obtained solid substance was dried at 50° C. under a reduced pressure and 3.6 g of 5-ethynylisophthalic acid was obtained (the yield: 99.5%).

[Preparation of 5-ethynylisophthalic acid dichloride from dipotassium 5-ethynylisophthalate]

Into a 2 liter four-necked flask equipped with a thermometer, a Dimroth condenser and a stirrer, 80 g (0.3 moles) of dipotassium 5-ethynylisophtalate and 400 milliliters of chloroform were placed and the resultant mixture was cooled at 0° C. To the cooled mixture, 391 g (4.5 moles) of thionyl chloride was added dropwise at a temperature of 5° C. or lower over 1 hour. Then, 4 ml of dimethylformamide and 4 g of hydroquinone were added and the resultant mixture was stirred at 45 to 50° C. for 3 hours. After the reaction mixture was cooled, formed crystals were removed by filtration and the removed crystals were washed with 150 ml of chloroform. The filtrate and the washing liquid were combined together and concentrated at a temperature of 40° C. or lower under a reduced pressure. The obtained residue was treated twice by extraction with 200 ml of diethyl ether and filtration. After removing diethyl ether from the extract under a reduced pressure, a semi-solid crude product was obtained. The crude product was washed with dry n-hexane and recrystallized from diethyl ether and 13 g of 5-ethynylisophthaloyl dichloride was obtained (the yield: 19%).

The data of the spectra of 5-ethynylisophthalic acid and ethynylisophthalic acid dichloride obtained above are shown in the following. These data support that the obtained compounds are the target compounds.

[5-Ethynylisophthalic acid ($C_{10}H_6O_4$)]

Appearance: white powder;
Melting point: 106.2° C. (DSC; 10° C./min)
$^1$H-NMR (400 MHz; DMSO-$d_6$): δ 8.16 (s, 2H); 8.45 (s, 1H)
$^{13}$C-NMR (100 MHz; DMSO-$d_6$): δ 81.5, 82.6, 122.7, 130.0, 131.9, 135.9, 165.7
IR (KBr; cm$^{-1}$):3272, 3081, 1797, 1741, 1438, 1265, 800, 761;
MS (FD) (m/z):190 (M$^+$)

| Elemental analysis: | | | |
|---|---|---|---|
| Calculated | C: 63.16%; | H: 3.18%; | O: 33.66% |
| Found | C: 63.24%; | H: 3.09%; | O: 33.67% |

[5-Ethynylisophthalic acid dichloride ($C_{10}H_4O_2Cl_2$)]

Appearance: white solid;
Melting point: 49° C. (DSC; 10° C./min);
$^1$H-NMR (400 MHz; CDCl$_3$): δ 8.47 (s, 2H), 8.77 (s, 1H);
$^{13}$C-NMR (100 MHz; CDCl$_3$): δ 80.0, 81.6, 124.9, 133.0, 134.7, 139.8, 166.6;
IR (KBr; cm$^{-1}$): 3465, 3077, 1766, 1736, 1151, 1022, 802, 740
MS (FD) (m/z): 190 (M$^+$–2Cl).

| Elemental analysis: | | | | |
|---|---|---|---|---|
| Calculated | C: 52.86%; | H: 1.77%; | Cl: 31.21%; | O: 14.08% |
| Found | C: 52.74%; | H: 1.70%; | Cl: 30.89%; | O: 14.67% |

EXAMPLE 2

[Preparation of 1-(3,5-bis(methoxycarbonyl)phenyl)-2-phenylethyne from dimethyl 5-trifluoromethanesulfonyloxyisophthalate]

Into a 1 liter four-necked flask equipped with a thermometer, a Dimroth condenser, an inlet for nitrogen and a stirrer, 125 g (0.365 moles) of dimethyl 5-trifluoromethanesulfonyloxyisophthalate obtained in accordance with the same procedures as those conducted in Example 1, 1.1 g (0.00419 moles) of triphenylphosphine, 0.275 g (0.00144 moles) of copper iodide and 40.95 g (0.401 moles) of ethynylbenzene were placed and nitrogen was introduced. To the obtained mixture, 375 ml of dehydrated triethylamine and 200 ml of dehydrated pyridine were added and dissolved under stirring. After the introduction of nitrogen was continued for 1 hour, 0.3 g (0.000427 moles) of dichlorobis(triphenylphosphine)palladium was quickly added and the resultant mixture was heated in an oil bath for 1 hour under the refluxing condition. Then, triethylamine and pyridine were removed by distillation under a reduced pressure and a viscous brown solution was obtained. The obtained solution was poured into 500 ml of water. The formed solid substance was separated by filtration and washed twice each with 500 ml of water, 500 ml of a 5 moles/liter hydrochloric acid and 500 ml of water. The solid substance was dried at 50° C. under a reduced pressure and 80.8 g of 1-(3,5-bis(methoxycarbonyl)-phenyl)-2-phenylethyne was obtained (the yield: 75%).

[Preparation of Dipotassium 5-(2-phenylethynyl) isophthalate from (3,5-bis(methoxycarbonyl)phenyl)-2-phenylethyne]

Into a 5 liter four-necked flask equipped with a thermometer, a Dimroth condenser and a stirrer, 3 liters of n-butanol and 180 g (2.72 moles) of potassium hydroxide (85%) were placed and dissolved by heating under the refluxing condition. To the obtained solution, 80 g (0.272 moles) of (3,5-bis(methoxycarbonyl)phenyl)-2-phenylethyne synthesized above was added and the resultant mixture was heated for 30 minutes under the refluxing condition. The reaction mixture was then cooled in an ice bath and the formed crystals were separated by filtration. The crystals were washed twice with 1 liter of ethanol and dried at 60° C. under a reduced pressure and 90.35 g of dipotassium 5-(2-phenylethynyl)-isophthalate was obtained (the yield: 97%).

[Preparation of 5-(2-phenylethynyl)isophthalic acid from dipotassium 5-(2-phentylethynyl)isophthalate]

Dipotassium 5-(2-phenylethynyl)isophthalate in an amount of 6.5 g (0.019 moles) was dissolved into 20 ml of ion-exchanged water and insoluble substances were removed by filtration with a 5C filter paper. To the obtained filtrate, a 5 moles/liter hydrochloric acid was added under stirring until the pH became 1. The formed solid substance was separated by filtration, washed with ion-exchanged water and filtered. The filtration and the washing were repeated twice. The obtained solid substance was dried at 50° C. under a reduced pressure and 5.0 g of 5-(2-phenylethynyl)isophthalic acid was obtained (the yield: 99.5%).

[Preparation of 5-(2-phenylethynyl)isophthalic acid dichloride from dipotassium 5-(2-phenylethynyl)isophthalate]

Into a 2 liter four-necked flask equipped with a thermometer, a Dimroth condenser and a stirrer, 82.1 g (0.24 moles) of dipotassium 5-(2-phenylethynyl)isophthalate and 400 liters of 1,2-dichloroethane were placed and the resultant mixture was cooled at 0° C. To the cooled mixture, 391 g (4.5 moles) of thionyl chloride was added dropwise at a temperature of 5° C. or lower over 1 hour. Then, 4 ml of dimethylformamide and 4 g of hydroquinone were added and the resultant mixture was stirred at 45 to 50° C. for 3 hours. After the reaction mixture was cooled, formed crystals were removed by filtration and the removed crystals were washed with 150 ml of chloroform. The filtrate and the washing liquid were combined together and concentrated at a temperature of 40° C. or lower under a reduced pressure. The obtained residue was treated twice by extraction with 200 ml of diethyl ether and filtration. Diethyl ether was removed from the extract under a reduced pressure and a semi-solid crude product was obtained. The crude product was washed with dry n-hexane and recrystallized from diethyl ether and 13.8 g of 5-(2-phenylethynyl)isophthalic acid dichloride was obtained (the yield: 19%).

The data of the spectra of 5-(2-phenylethynyl)isophthalic acid and 5-(2-phenylethynyl)isophthalic acid dichloride obtained above are shown in the following. These data support that the obtained compounds are the target compounds.

[5-(2-Phenylethynyl)isophthalic acid ($C_{16}H_{10}O_4$)]
Appearance: white powder;
Melting point: 99.7° C. (DSC; 10° C./min);
$^1$H-NMR (400 MHz; $(CD_3)_2CO$): δ 7.44 (s, 3H), 7.64 (m, 2H), 8.35 (d, 2H, J=1.6 Hz), 8.63 (t, 1H, J=1.6 Hz);
$^{13}$C-NMR (100 MHz; $(CD_3)_2CO$): δ 88.0, 91.7, 123.2, 125.0, 129.5, 129.5, 129.9, 131.0, 132.5, 132.7, 132.7, 136.8, 166.2;
IR (KBr; cm$^{-1}$): 3549, 2968, 2365, 1722, 1492, 1446, 1276, 917, 756, 674;
MS (FD) (m/z): 266 (M$^+$).

| Elemental analysis: | | | |
|---|---|---|---|
| Calculated | C: 72.18%; | H: 3.79%; | O: 24.04% |
| Found | C: 70.86%; | H: 3.64%; | O: 25.50% |

[5(2- Phenylethynyl)isophthalic acid dichloride ($C_{16}H_8O_2Cl_2$)]
Appearance: white solid;
Melting point: 124° C. (DSC; 10° C./min);
$^1$H-NMR (400 MHz; $CDCl_3$): δ 7.40 (m, 3H), 7.57 (m, 2H), 8.50 (d, 2H, J=1.6 Hz), 8.73 (t, 2H, J=1.6 Hz);
$^{13}$C-NMR (100 MHz; $CDCl_3$): δ 85.7, 93.6, 121.6, 126.2, 128.6, 129.5, 131.9, 132.2, 134.6, 139.2, 166.8;
IR (KBr; cm$^{-1}$): 3489, 3075, 2216, 1756, 1580, 1489, 1440, 1329, 1218, 1145, 1000, 819, 690;
MS (FD) (m/z): 266 (M$^+$-2Cl).

| Elemental analysis: | | | | |
|---|---|---|---|---|
| Calculated | C: 63.39%; | H: 2.66%; | Cl: 23.39%; | O: 10.56% |
| Found | C: 63.04%; | H: 2.49%; | Cl: 22.69%; | O: 11.78% |

EXAMPLE 3

[Preparation of 5-bromoisophthalic acid]

Into a 1 liter four-necked flask equipped with a thermometer, a stirrer and a dropping funnel, 99.18 g (0.55 moles) of 5-hydroxyisophthalic acid, 165 ml of a 48% by weight hydrobromic acid and 150 ml of distilled water were placed and the resultant mixture was stirred. The flask was cooled at a temperature of 5° C. or lower. To the cooled mixture, a solution prepared by dissolving 39.4 g (0.57 moles) of sodium nitrite into 525 ml of distilled water was added dropwise over 1 hour and an aqueous solution of a diazonium salt was obtained. Into a 3-liter four-necked flask equipped with a thermometer, a Dimroth condenser, a dropping funnel and a stirrer, 94.25 g (0.66 moles) of cuprous chloride and 45 ml of a 48% by weight hydrobromic acid were placed and the resultant mixture was stirred. The flask was cooled at a temperature of 0° C. or lower and the aqueous solution of the diazonium salt prepared above was added dropwise over 2 hours. After the addition was completed, the resultant mixture was stirred at the room temperature for 30 minutes and heated for 30 minutes under the refluxing condition. After the reaction mixture was cooled by being left standing, the formed precipitates were separated by filtration and washed twice with 2 liters of distilled water. The obtained white solid substance was dried under a reduced pressure at 50° C. for 2 days and 117 g of a crude product was obtained. The obtained crude product was used for the next step without purification.

[Preparation of dimethyl 5-bromoisophthalate from 5-bromoisophthalic acid]

Into a 500 ml flask equipped with a stirrer and a Dimroth condenser, 110 g of 5-bromoisophthalic acid obtained above, 500 ml of methanol and 10 g of a concentrated sulfuric acid were placed and the resultant mixture was heated under the refluxing condition for 6 hours. After the reaction mixture was cooled by being left standing, the cooled mixture was added dropwise to 1 liter of distilled water and the obtained mixture was neutralized with a 5% by weight aqueous solution of sodium hydrogencarbonate. The formed precipitates were separated by filtration and washed twice with 2 liters of distilled water. The obtained white solid substance was dried at 50° C. under a reduced pressure for 2 days and 109 g (0.4 moles) of dimethyl 5-bromoisophthalate was obtained (the yield: 89%).

[Preparation of 4-(3,5-bis(methoxycarbonyl)phenyl)-2-methyl-3-butyn-1-ol from dimethyl 5-bromoisophthalate]

In accordance with the same procedures as those conducted in Example 1 except that 99.7 g (0.365 moles) of dimethyl 5-bromoisophthalate was used in place of 125 g (0.365 moles) of dimethyl 5-trifluoromethanesulfonyloxyisophthalate, 98.9 g of 4-(3,5-bis(methoxy-carbonyl)phenyl)-2-methyl-3-butyn-1-ol from dimethyl 5-bromo-isophthalate was obtained (the yield: 98%).

The same procedures as those conducted in Example 1 were conducted in the succeeding steps and dipotassium salt of 5-ethynylisophthalic acid, 5-ethynylisophthalic acid and 5-ethynyl-isophthalic acid dichloride were obtained. The appearance and the data of the melting points, the spectra of $^1$H-NMR, $^{13}$C-NMR, IR, MS and the elemental analysis of 5-ethynylisophthalic acid and 5-ethynylisophthalic acid dichloride all agreed with those in Example 1 and it was shown that the same compounds as those in Example 1 were obtained.

EXAMPLE 4

[Preparation of 1-(3,5-bis(methoxycarbonyl)phenyl)-2-phenylethyne]

In accordance with the same procedures as those conducted in Example 2 except that 99.7 g (0.365 moles) of dimethyl 5-bromo-isophthalate obtained in accordance with the same procedures as those conducted in Example 3 was used in place of 125 g (0.365 moles) of dimethyl 5-trifluoromethanesulfonyloxyisophthalate, 80.8 g of 1-(3,5-bis(methoxycarbonyl)phenyl)-2-phenylethyne was obtained.

The same procedures as those conducted in Example 2 were conducted in the succeeding steps and dipotassium salt of 5-(2-phenylethynyl)isophthalic acid, 5-(2-phenylethynyl)isophthalic acid and 5-(2-phenylethynyl)isophthalic acid dichloride were obtained. The appearance and the data of the melting points, the spectra of $^1$H-NMR, $^{13}$C-NMR, IR, MS and the elemental analysis of 5-(2-phenylethynyl)-isophthalic acid and 5-(2-phenylethynyl)isophthalic acid dichloride all agreed with those in Example 2 and it was shown that the same compounds as those in Example 2 were obtained.

EXAMPLE 5

[Preparation of dimethyl 5-(4-nitrophenoxy)isophthalate]

Into a 2 liter four-necked flask equipped with a thermometer, a stirrer and a Dean Stark distillation apparatus, 133.24 g (0.63 moles) of dimethyl 5-hydroxyisophthalate, 107.33 g (0.76 moles) of 4-fluoronitrobenzene, 60 ml of N,N-dimethylformamide and 190 ml of toluene were placed. The resultant mixture was stirred at 165° C. for 4 hours while water formed as the byproduct was removed by azeotropic distillation. After cooling, the obtained reaction mixture was poured into 3 liters of ion-exchanged water and the product was precipitated. The formed precipitates were separated by filtration and washed with ion-exchanged water and ethanol. The obtained light yellow solid substance was dried under a reduced pressure at 50° C. for 1 day and 142.01 g of a product was obtained (the yield: 68%).

[Preparation of dimethyl 5-(4-aminophenoxy)isophthalate]

Into a 1 liter flask having an egg plant shape, 66.24 g (0.2 moles) of dimethyl 5-(4-nitrophenoxy)isophthalate obtained above, 6.39 g of a 10% by weight palladium-active carbon, 440 ml of tetrahydrofuran and 220 ml of ethanol were placed and the resultant mixture was stirred for 24 hours under the atmosphere of hydrogen. The reaction liquid was filtered with Celite and the filtrate was concentrated under a reduced pressure. Hexane was added to the concentrated filtrate and the formed precipitates were separated by filtration. The obtained white solid substance was dried at 50° C. for 1 day under a reduced pressure and 55.96 g of a product was obtained (the yield: 93%).

[Preparation of dimethyl 5-(4-iodophenoxy)isophthalate]

Into a 1 liter four-necked flask equipped with a thermometer, a stirrer and a dropping funnel, 450 ml of ion-exchanged water, 75 ml of a concentrated sulfuric acid and 45.20 g (0.15 moles) of dimethyl 5-(4-aminophenoxy)isophthalate obtained above were placed and the resultant mixture was stirred. The flask was cooled at a temperature of 5° C. or lower. Into the cooled flask, a solution prepared by dissolving 12.42 g (0.18 moles) of sodium nitrite into 25 ml of ion-exchanged water was added dropwise over 20 minutes. The resultant mixture was stirred at a temperature of 5° C. or lower for 40 minutes and an aqueous solution of a diazonium salt was obtained. To the obtained solution, a solution prepared by dissolving 27.39 g (0.165 moles) of potassium iodide into 33 ml of ion-exchanged water was added and the resultant mixture was stirred at a temperature of 5° C. or lower for 1 hour and at the room temperature for 1 hour. The formed precipitates were separated by filtration and dissolved into 300 ml of ethyl acetate. The obtained solution was washed twice with 200 ml of a 10% by weight aqueous solution of sodium hydrogensulfite and twice with 200 ml of ion-exchanged water. After the organic layer was dried with anhydrous magnesium sulfate, the solvent was removed by distillation under a reduced pressure and a brown crude product was separated by adding a small amount of hexane. The crude product was treated by extraction with hexane using a Soxhlet extractor and, after the removal of the solvent by distillation, recrystallized from methanol and a light yellow solid substance was obtained. The solid substance was separated by filtration and dried at 50° C. for 1 day under a reduced pressure and 25.40 g of a product was obtained (the yield: 41%).

[Preparation of dimethyl 5-(4-(2-phenylethynyl)phenoxy) isophthalate]

Into a 500 ml four-necked flask equipped with a thermometer, a Dimroth condenser and an inlet for nitrogen, 24.73 g (0.06 moles) of dimethyl 5-(4-iodophenoxy) isophthalate obtained above, 0.79 g (0.003 moles) of triphenylphosphine, 0.23 g (0.0012 moles) of copper iodide, 6.74 g (0.066 moles) of ethynylbenzene, 72 ml of dehydrated triethylamine, 38 ml of dehydrated pyridine and 0.25 g (0.00036 moles) of dichlorobis-(triphenylphosphine) palladium were placed and the resultant mixture was heated under the refluxing condition of 105° C. for 1 hour under the stream of nitrogen. Triethylamine and pyridine were removed by distillation under a reduced pressure and a viscous brown solution was obtained. To the obtained solution, 200 ml of water and 5 ml of hydrochloric acid were added. The formed solid substance was separated by filtration and washed with 500 ml of water. The solid substance was dried at 50° C. 1 day under a reduced pressure and 17.39 g of a product was obtained (the yield: 75%).

[Preparation of dipotassium 5-(4-(2-phenylethynyl) phenoxy)isophthalate]

Into a 1 liter flask having an egg plant shape, 450 ml of n-butanol and 47.53 g (0.32 moles) of potassium hydroxide (85% by weight) were placed and potassium hydroxide was dissolved into n-butanol by heating under a refluxing condition. To the obtained solution, 15.46 g (0.04 moles) of dimethyl 5(4-(2-phenylethynyl)phenoxy)isophthalate obtained above was added and the resultant mixture was heated for 30 minutes under the refluxing condition. The obtained mixture was cooled in an ice bath and the formed crystals were separated by filtration. The crystals were washed twice with 200 ml of isopropanol, separated by filtration and dried at 50° C. under a reduced pressure and 16.86 g of a product was obtained (the yield: 97%).

[Preparation of 5-(4-(2-phenylethynyl)phenoxy)isophthalic acid from dipotassium 5-(4-(2-phenylethynyl)phenoxy) isophthalate]

Dipotassium 5-(4-(2-phenylethynyl)phenoxy) isophthalate obtained above in an amount of 8.69 g (0.02 moles) was dissolved into 40 ml of ion-exchanged water and insoluble substances were removed by filtration with a 5C filter paper. To the obtained filtrate, hydrochloric acid was added under stirring until the pH became 1. The formed solid substance was separated by filtration, washed with ion-exchanged water and filtered. The washing with ion-exchanged water and the filtration were repeated twice. The obtained solid substance was dried at 50° C. under a reduced pressure and 6.88 g of a product was obtained (the yield: 96%).

[Preparation of 5-(4-(2-phenylethynyl)phenoxy)isophthalic acid dichloride from dipotassium 5-(4-(2-phenylethynyl) phenoxy)isophthalate]

Into a 500 ml four-necked flask equipped with a thermometer and a Dimroth condenser, 15.2 g (0.035 moles) of dipotassium 5-(4-(2-phenylethynyl)phenoxy)isophthalate obtained above and 90 ml of chloroform were placed and the resultant mixture was cooled at 0° C. To the cooled mixture, 62.46 g (0.525 moles) of thionyl chloride was added dropwise at a temperature of 5° C. or lower over 15 minutes. Then, 0.7 ml of dimethylformamide and 0.7 g of hydroquinone were added and the resultant mixture was stirred at 45 to 50° C. for 3 hours. After the reaction mixture was cooled, formed crystals were removed by filtration and the removed crystals were washed with 50 ml of chloroform. The filtrate and the washing liquid were combined together and concentrated at a temperature of 40° C. or lower under a reduced pressure. The obtained residue was treated by extraction and recrystallization using hot n-hexane. The obtained solid substance was dried under a reduced pressure and 3.44 g of a product was obtained (the yield: 25%).

[Preparation of 5-(4-(2-phenylethynyl)phenoxy)isophthalic acid dichloride from 5-(4-(2-phenylethynyl)phenoxy) isophthalic acid]

Into a 500 ml four-necked flask equipped with a thermometer and a Dimroth condenser, 12.54 g (0.035 moles) of 5-(4-(2-phenylethynyl)-phenoxy)isophthalic acid obtained above, 100 ml of 1,2-dichloroethane, 9.16 g (0.077 moles) of thionyl chloride and 8.0 mg (0.00035 moles) of benzyltriethylammonium chloride were placed and the resultant mixture was heated for 3 hours under the refluxing condition. The obtained solution was filtered while the solution was hot. After the filtrate was concentrated by removing the solvent under a reduced pressure, n-hexane was added to the concentrated solution and crystals were formed. The obtained solid substance was dried under a reduced pressure and 6.33 g of a product was obtained (the yield: 46%).

The data of the spectra of 5-(4-(2-phenylethynyl) phenoxy)-isophthalic acid and 5-(4-(2-phenylethynyl) phenoxy)isophthalic acid dichloride obtained above are shown in the following. These data support that the obtained compounds are the target compounds.

[5-(4- (2-Phenylethynyl)phenoxy)isophthalic acid $(C_{22}H_{14}O_5)$]

Appearance: white powder;
Melting point: not found at 320° C. or lower (DSC; 10° C./min);
$^1$H-NMR (400 MHz; DMSO-d6): δ 13.47 (br), 8.25 (s, 1H), 7.71; (s, 2H), 7.61 (d, 2H), 7.53 (m, 2H), 7.40 (m, 3H), 7.13 (d, 2H);
$^{13}$C-NMR (100 MHz; DMSO-d6): δ 166.12, 156.96, 156.29, 133.79, 133.54, 131.54, 128.95, 125.29, 123.11, 122.51, 119.82, 118.45, 89.37, 88.90;
IR (KBr; cm$^{-1}$): 3424, 2826, 2568, 1713, 1589, 1504, 1466, 1419, 1322, 1284, 1241, 1206, 1165, 1102, 977, 846, 758, 691;
MS (FD) (m/z): 358.2 (M$^+$);

| Elemental analysis: | | |
|---|---|---|
| Calculated | C: 73.74%; | H: 3.94% |
| Found | C: 73.31%; | H: 3.84% |

[5-(4-(2-Phenylethynyl)phenoxy)isophthalic acid dichloride]

Appearance: slightly yellow solid
Melting point: 130° C. (DSC; 10° C. /min);
$^1$H-NMR (400 MHz; CDCl$_3$): δ 8.56 (s, 2H), 7.89 (s, 2H), 7.59 (d, 2H), 7.52 (m, 2H), 7.35 (m, 3H), 7.04 (d, 2H);
$^{13}$C-NMR (100 MHz; CDCl$_3$): δ 166.65, 158.27, 154.82, 135.78, 133.77, 131.54, 128.41, 128.35, 127.90, 125.96, 122.87, 120.40, 119.54, 89.84, 88.14;
IR (KBr; cm$^{-1}$): 3446, 1754, 1588, 1506, 1443, 1202, 1218, 1145, 991, 846, 824, 764, 737, 694, 683;
MS (FD) (m/z): 394.2 (M$^+$).

| Elemental analysis: | | | |
|---|---|---|---|
| Calculated | C: 67.20%; | H: 3.08%; | Cl: 17.52% |
| Found | C: 66.65%; | H: 2.99%; | Cl: 17.99% |

EXAMPLE 6

[Preparation of dimethyl 5-(4-hydroxyphenoxy) isophthalate]

Into a 1 liter four-necked flask equipped with a thermometer, a stirrer and a dropping funnel, 450 ml of ion-exchanged water, 75 ml of a concentrated sulfuric acid and 45.20 g (0.15 moles) of dimethyl 5-(4-aminophenoxy) isophthalate obtained in accordance with the same procedures as those conducted in Example 5 were placed and the resultant mixture was stirred. The flask was cooled at a temperature of 50° C. or lower. Into the cooled flask, a solution prepared by dissolving 12.42 g (0.18 moles) of sodium nitrite into 25 ml of distilled water was added dropwise over 20 minutes. The resultant mixture was stirred at a temperature of 5° C. or lower for 40 minutes and at 100° C. for 2 hours. The formed precipitates were separated by filtration and, after a treatment with active carbon in methanol, recrystallized from methanol. The formed solid substance was separated by filtration and dried at 50° C. for 1 day under a reduced pressure and 23.58 g of a product was obtained (the yield: 52%).

[Preparation of dimethyl 5-(4-trifluoromethanesulfonyloxyphenoxy)-isophthalate]

Into a 1 liter four-necked flask equipped with a thermometer, a Dimroth condenser, a calcium chloride tube and a stirrer, 21.26 g (0.07 moles) of dimethyl 5-(4-hydroxyphenoxy)isophthalate obtained above, 300 ml of dehydrated toluene and 16.61 g (0.21 moles) of dehydrated pyridine were placed and the resultant mixture was cooled at −30° C. under stirring. To the cooled mixture, 39.50 g (0.14 moles) of anhydrous trifluoro-methanesulfonic acid was slowly added dropwise with sufficient care so that the temperature did not exceed −25° C. After the addition was completed, the temperature was elevated at 0° C. and the reaction was allowed to proceed for 1 hour. Then, the temperature was elevated to the room temperature and the reaction was allowed to proceed for 5 hours. The obtained reaction mixture was poured into 400 ml of ice water and separated into an aqueous layer and an organic layer. The aqueous layer was treated twice by extraction with 100 ml of toluene and the extract was combined with the organic layer. The obtained organic layer was washed twice with 300 ml of water and dried with anhydrous magnesium sulfate. From the resultant mixture, the solvent was removed by distillation under a reduced pressure and the obtained product was recrystallized from hexane. The solid product separated by filtration was dried at 50° C. for 1 day under a reduced pressure and 26.14 g of a product was obtained (the yield: 86%).

[Preparation of dimethyl 5-(4-(2-phenylethynyl)phenoxy) isophthalate]

In accordance with the same procedures as those conducted in Examples 5 except that 26.06 g (0.06 moles) of 5-(4-trifluoromethane-sulfonyloxyphenoxy)isophthalate was used in place of 24.73 g (0.06 moles) of dimethyl 5-(4-iodophenoxy)isophthalate used in Example 5, dimethyl 5-(4-(2-phenylethynyl)phenoxy)isophthalate was obtained.

The same procedures as those conducted in Example 5 were conducted in the succeeding steps and dipotassium 5-(4-(2-phenylethynyl)-phenoxy)isophthalate, 5-(4-(2-phenylethynyl)phenoxy)isophthalic acid and 5-(4-(2-phenylethynyl)phenoxy)isophthalic acid dichloride were obtained. The appearance and the data of the melting points, the spectra of $^1$H-NMR, $^{13}$C-NMR, IR, MS and the elemental analysis of 5-(4-(2-phenylethynyl)-phenoxy)isophthalic acid and 5-(4-(2-phenylethynyl)phenoxy)isophthalic acid dichloride all agreed with those in Example 5 and it was shown that the same compounds as those in Example 5 were obtained.

INDUSTRIAL APPLICABILITY

In accordance with the present invention, aromatic carboxylic acids and acid halide derivatives thereof which are useful as the raw material for macromolecular compounds and, in particular, for polycondensed macromolecular compounds exhibiting excellent heat resistance can be easily provided.

What is claimed is:

1. An aromatic carboxylic acid having a structure represented by formula (1):

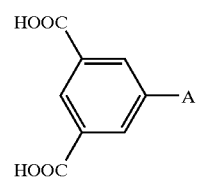

wherein A represents a group represented by formula (a) or (b):

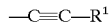

$R^1$ in formula (a) representing hydrogen atom, an alkyl group selected from the group consisting of ethyl group, propyl group and butyl group or an aromatic group selected from the group consisting of phenyl group, naphtyl group, anthryl group, quinolyl group and quinoxalyl and $R^2$ in formula (b) representing an alkyl group selected from the group consisting of phenyl group, naphtyl group, anthryl group, quinolyl group and quinoxalyl.

2. An acid halide derivative of an aromatic carboxylic acid having a structure represented by formula (2):

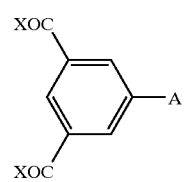

wherein A represents a group represented by formula (a) or (b):

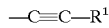

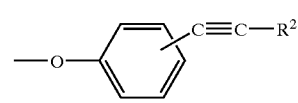

$R^1$ in formula (a) representing hydrogen atom, an alkyl group selected from the group consisting of ethyl group, propyl group and butyl group or an aromatic group selected from the group consisting of phenyl group, naphtyl group, anthryl group, quinolyl group and quinoxalyl and $R^2$ in formula (b) representing an alkyl group selected from the group consisting of ethyl group, propyl group and butyl group or an aromatic group selected from the group consisting of phenyl group, naphtyl group, anthryl group, quinolyl group and quinoxalyl; and X represents a halogen atom.

3. The acid halide derivative of an aromatic carboxylic acid according to claim 2, wherein X in formula (2) represents chlorine atom.

4. A process for producing an aromatic carboxylic acid represented by formula (1-1):

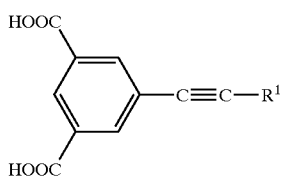

(1-1)

wherein $R^1$ represents hydrogen atom, an alkyl group selected from the group consisting of ethyl group, propyl group and butyl group or an aromatic group selected from the group consisting of phenyl group, naphtyl group, anthryl group, quinolyl group and quinoxalyl, the process comprising:

obtaining a compound represented by formula (5):

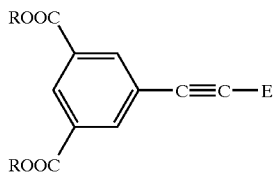

(5)

wherein R represents a lower alkyl group and E represents a protective group selected from the group consisting of trimethylsilyl group, hydroxypropyl group, or a substituent selected from the group consisting of an alkyl group selected from the group consisting of ethyl group, propyl group and butyl group or an aromatic group selected from the group consisting of phenyl group, naphtyl group, anthryl group, quinolyl group and quinoxaly, by reacting a compound represented by formula (3):

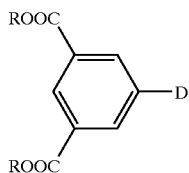

(3)

wherein D represents a group which is easily eliminated from the aromatic ring by a coupling reaction of the compound represented by formula (3) and a compound represented by formula (4), said group D being selected from the group consisting of fluorine, chlorine, bromine, iodine and trifluoromethanesulfonyloxy and R is as defined, in formula (5) with a compound represented by formula (4):

(4)

wherein E is as defined, in formula (5);

forming a compound represented by formula (6):

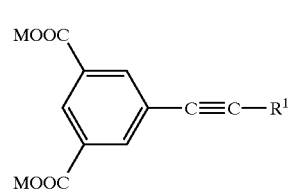

(6)

wherein $R^1$ is as defined in formula (1-1) and M represents an alkali metal, by treating the obtained compound represented by formula (5) in a presence of an alkali metal hydroxide; and treating the formed compound represented by formula (6) with an acid.

5. The process for producing an aromatic carboxylic acid according to claim 4, wherein a transition metal catalyst is used for the reaction of the compound represented by formula (3) and the compound represented by formula (4).

6. A process for producing an aromatic carboxylic acid represented by formula (1-2):

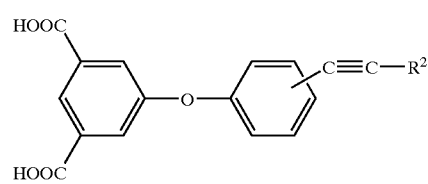

(1-2)

wherein $R^2$ represents an alkyl group selected from the group consisting of ethyl group, propyl group and butyl group or an aromatic group selected from the group consisting of phenyl group, naphtyl group, anthryl group, quinolyl group and quinoxaly, the process comprising:

obtaining a compound represented by formula (9):

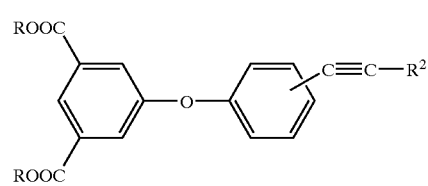

(9)

wherein R represents a lower alkyl group and $R^2$ is as defined in formula (1-2), by reacting a compound represented by formula (7):

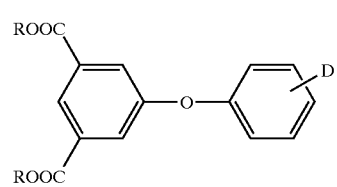

(7)

wherein D represents a group which is easily eliminated from the aromatic ring by a coupling reaction of the compound represented by formula (7) and a compound represented by formula (8), said group D being selected from the group consisting of fluorine, chlorine, bromine, iodine and trifluoromethanesulfonyloxy and R is as defined in formula (9), with a compound represented by formula (8):

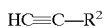  (8)

wherein $R^2$ is as defined in formula (9);

forming a compound represented by formula (10):

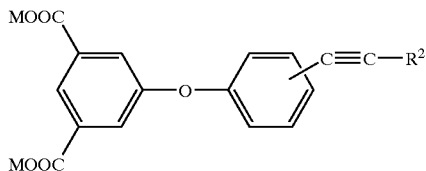  (10)

wherein M represents an alkali metal and $R^2$ is as defined in formula (9), by treating the obtained compound represented by formula (9) in a presence of an alkali metal hydroxide; and treating the formed compound represented by formula (10) with an acid.

7. The process for producing an aromatic carboxylic acid according to claim 6, wherein a transition metal catalyst is used for the reaction of the compound represented by formula (7) and the compound represented by formula (8).

8. A process for producing an acid halide derivative of an aromatic carboxylic acid represented by formula (2-1):

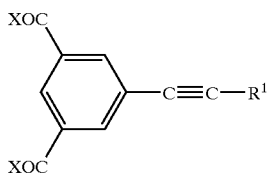  (2-1)

wherein X represents a halogen atom and $R^1$ represents hydrogen atom, an alkyl group selected from the group consisting of ethyl group, propyl group and butyl group or an aromatic group selected from the group consisting of phenyl group, naphtyl group, anthryl group, quinolyl group and quinoxaly, the process comprising:

treating with a halogenating agent a compound represented by formula (1-1):

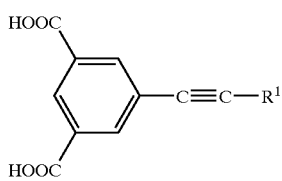  (1-1)

wherein $R^1$ is as defined in formula (2-1), or a compound represented by formula (6):

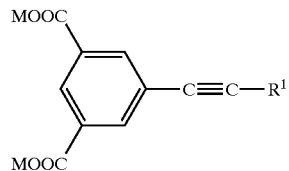  (6)

wherein M represents an alkali metal and $R^1$ is as defined in formula (2-1).

9. The process for producing an acid halide derivative of an aromatic carboxylic acid according to claim 8, wherein the halogenating agent is a chlorinating agent and X in formula (2-1) represents chlorine atom.

10. A process for producing an acid halide derivative of an aromatic carboxylic acid represented by formula (2-2):

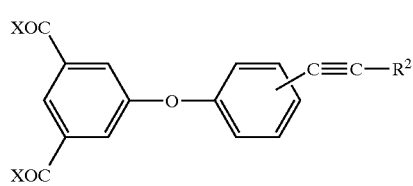  (2-2)

wherein X represents a halogen atom and $R^2$ represents an alkyl group selected from the group consisting of ethyl group, propyl group and butyl group or an aromatic group selected from the group consisting of phenyl group, naphtyl group, anthryl group, quinolyl group and quinoxaly, the process comprising:

treating with a halogenating agent a compound represented by formula (1-2):

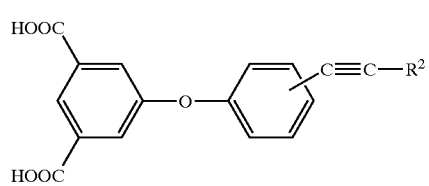  (1-2)

wherein $R^2$ is as defined in formula (2-2), or a compound represented by formula (10):

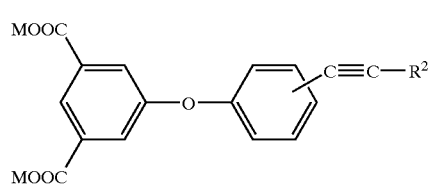  (10)

wherein M represents an alkali metal and $R^2$ is as defined in formula (2-2).

11. The process for producing an acid halide derivative of an aromatic carboxylic acid according to claim 10, wherein the halogenating agent is a chlorinating agent and X in formula (2-2) represents chlorine atom.

* * * * *